United States Patent [19]

Philipp et al.

[11] 4,177,284
[45] Dec. 4, 1979

[54] 2-SUBSTITUTED-3-METHYL-γ-PYRONE TRICVCLIC DERIVATIVES AND PROCESS THEREFOR

[75] Inventors: Adolf H. Philipp, St. Laurent; Ivo L. Jirkovsky, Montreal, both of Canada

[73] Assignee: Ayerst McKenna & Harrison Ltd., Montreal, Canada

[21] Appl. No.: 855,538

[22] Filed: Nov. 28, 1977

[51] Int. Cl.² .................... A61K 31/38; C07D 495/04
[52] U.S. Cl. .................... 424/275; 424/269; 548/253; 549/26; 549/27; 260/345.2
[58] Field of Search .................... 424/275; 260/327 TH

[56] References Cited

U.S. PATENT DOCUMENTS

| | | | |
|---|---|---|---|
| 3,816,467 | 6/1974 | Wright | 260/345.7 |
| 3,855,216 | 12/1974 | Kaminsky et al. | 260/243 R |
| 3,862,144 | 1/1975 | Kaminsky | 260/345.2 |
| 4,060,619 | 11/1977 | Philipp et al. | 424/256 |

OTHER PUBLICATIONS

Dean et al., *J. Chem. Soc.*, Chem. Comm., (1974), pp. 440-441.

*Primary Examiner*—John D. Randolph
*Attorney, Agent, or Firm*—Arthur E. Wilfond

[57] ABSTRACT

Compounds of formula I

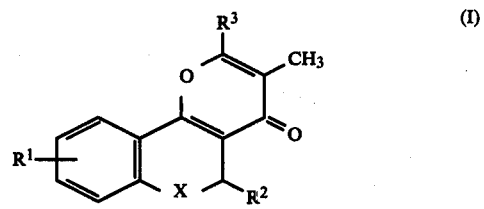

in which $R^1$ is hydrogen, halogen, nitro, trifluoromethyl, lower alkyl or lower alkoxy; $R^2$ is hydrogen or lower alkyl; $R^3$ is hydroxy, 1H-tetrazol-5-yl or $COOR^4$ wherein $R^4$ is hydrogen or lower alkyl, and X is O, S, SO or $SO_2$, are disclosed. The compounds of formula I are useful for treating allergic conditions. Methods for the preparation and use of the compounds are disclosed.

15 Claims, No Drawings

2-SUBSTITUTED-3-METHYL-γ-PYRONE TRICVCLIC DERIVATIVES AND PROCESS THEREFOR

BACKGROUND OF THE INVENTION (a) Field of the Invention

This invention relates to novel 2-substituted-3-methyl-γpyrone tricyclic derivatives, to processes for their preparation, to methods for using said derivatives, and to pharmaceutically acceptable compositions of said derivatives.

More specifically, the present invention relates to novel 2-substituted-3-methyl-γ-pyrone tricyclic derivatives possessing valuable pharmacologic properties. For example, these derivatives are useful for treating allergic conditions at dosages which do not elicit undesirable side effects. The combination of these pharmacologic properties together with a low order of toxicity render the 2-substituted-3-methyl-γ-pyrone tricyclic derivatives of the invention therapeutically useful.

(b) Description of the Prior Art

A number of reports dealing with fused γ-pyrone-tricyclic derivatives are available. One report concerns fused γ-pyrone-2-carboxylic acid derivatives of benzofuran, as described by J. B. Wright, U.S. Pat. No. 3,816,467, issued June 11, 1974. Fused γ-pyrone-2-methyl derivatives of benzopyran have been prepared by F. M. Dean, et al., J. Chem. Soc., Chem. Comm., 440(1974), in order to prepare the pyranopyrone nucleus of the fungal metabolite citromycetin. A number of pyrano (3,2-c) (1,2)benzothiazine-6,6-dioxide derivatives are reported by D. Kaminsky et al. in U.S. Pat. No. 3,855,216, issued Dec. 17, 1974. Recently, fused γ-pyrone-3-carboxaldehyde derivatives of dihydronaphthol have been prepared by D. Kaminsky, U.S. Pat. No. 3,862,144, issued Jan. 21, 1975. The compounds of the present invention are distinguished from the prior art compounds by having substituents at a variety of positions to the γ-pyrone tricyclic nucleus, most notably a methyl group at position 3 and a substituent at 2 as well as having hetero atoms in positions 1 and 6 of the tricyclic nucleus.

In copending U.S. Pat. Application, Ser. No. 649,113, filed Jan. 14, 1976 and now issued as U.S. Pat. No. 4,060,619 on Nov. 29, 1977, γ-pyrone tricyclic derivatives, which differ most notably from the compounds of this invention by lacking a methyl substituent at position C-3 of the tricyclic system, are disclosed. In addition, it should be noted that the use of the processes described therein, with appropriately substituted reactants to obtain the compounds of the present invention, is not suitable for preparing the present compounds, since the required substituted reactants cannot be obtained in the practical yields.

Furthermore, a noteworthy feature of the present process involves a novel reaction for converting a γ-pyrone derivative with a functionality at C-3 into a derivatives functionalized at C-2. The reaction comprises an allylic type of rearrangement which occurs when the active ester portion, i.e., the 3-chloromethyl, 3-bromomethyl, 3-fluoromethyl or mesylated hydroxy methyl portion, reacts with cyanide ion whereby functionality at C-2 is introduced. In the field of heterocyclic chemistry in which oxygen is the sole heteroatom of the ring system this type of reaction is unknown.

SUMMARY OF THE INVENTION

The compounds of this invention are represented by formula I

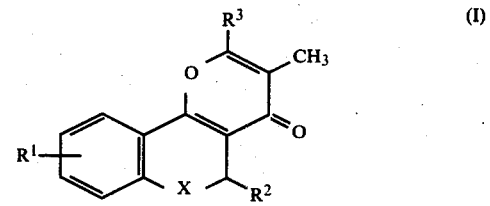

in which $R^1$ is hydrogen, halogen, nitro, trifluoromethyl, lower alkyl or lower alkoxy; $R^2$ is hydrogen or lower alkyl; $R^3$ is hydroxy, IH-tetrazol-5-yl or $COOR^4$ wherein $R^4$ is hydrogen or lower alkyl, and X is O, S, SO or $SO_2$.

A preferred group of compounds are represented by formula I in which $R^1$ is hydrogen, halogen, nitro, trifluoromethyl, lower alkyl or lower alkoxy; $R^2$ is hydrogen or lower alkyl; $R^3$ is hydroxy, 1H-tetrazol-5-yl or $COOR^4$ wherein $R^4$ is hydrogen or lower alkyl, and X is O.

A preferred group of compounds are represented by formula I in which $R^1$ is hydrogen, halogen nitro, trifluoromethyl, lower alkyl or lower alkoxy; $R^2$ is hydrogen or lower alkyl; $R^3$ is hydroxy, 1H-tetrazol-5-yl or $COOR^4$ wherein $R^4$ is hydrogen or lower alkyl, and X is S, SO or $SO_2$.

Another preferred group of compounds are represented by formula I in which $R^1$ is hydrogen, halogen, nitro, trifluoromethyl, lower alkyl or lower alkoxy; $R^2$ is hydrogen or lower alkyl; $R^3$ is 1H-tetrazol-5-yl and X is O.

Another preferred group of compounds are represented by formula I in which $R^1$ is hydrogen, halogen, nitro, trifluoromethyl, lower alkyl or lower alkoxy; $R^2$ is hydrogen or lower alkyl; $R^3$ is 1H-tetrazol-5-yl and X is S, SO or $SO_2$.

Another preferred group of compounds are represented by formula I in which $R^1$ is hydrogen, halogen, nitro, trifluoromethyl, lower alkyl or lower alkoxy; $R^2$ is hydrogen or lower alkyl; $R^3$ is hydroxy and X is O.

Another preferred group of compounds are represented by formula I in which $R^1$ is hydrogen, halogen, nitro, trifluoromethyl, lower alkyl or lower alkoxy; $R^2$ is hydrogen or lower alkyl; $R^3$ is hydroxy and X is S, SO or $SO_2$.

Another preferred group of compounds are represented by formula I in which $R^1$ is hydrogen, halogen, nitro, trifluoromethyl, lower alkyl or lower alkoxy; $R^2$ is hydrogen or lower alkyl; $R^3$ is $COOR^4$ wherein $R^4$ is hydrogen or lower alkyl and X is O.

Another preferred group of compounds are represented by formula I in which $R^1$ is hydrogen, halogen, nitro, trifluoromethyl, lower alkyl or lower alkoxy; $R^2$ is hydrogen or lower alkyl; $R^3$ is $COOR^4$ wherein $R^4$ is hydrogen or lower alkyl and X is S, SO or $SO_2$.

A more preferred group of compounds are represented by formula I in which $R^1$ and $R^2$ are hydrogen; $R^3$ is hydroxy, 1H-tetrazol-5-yl or $COOR^4$ wherein $R^4$ is hydrogen or lower alkyl, and X is O, S or $SO_2$.

Another more preferred group of compounds are represented by formula I in which $R^1$ and $R^2$ are hydrogen, $R^3$ is hydroxy, 1H-tetrazol-5-yl or $COOR^4$ wherein $R^4$ is hydrogen or lower alkyl and X is O.

Another more preferred group of compounds are represented by formula I in which $R^1$ and $R^2$ are hydrogen, $R^3$ is hydroxy, 1H-tetrazol-5-yl or $COOR^4$ wherein $R^4$ is hydrogen or lower alkyl and X is S or $SO_2$.

A particularly preferred group of compounds are represented by formula I in which $R^1$ and $R^2$ are hydrogen; $R^3$ is 1H-tetrazol-5-yl or $COOR^4$ wherein $R^4$ is hydrogen and X is O, or S or $SO_2$.

Another particularly preferred group of compounds are represented by formula I in which $R^1$ and $R^2$ are hydrogen; $R^3$ is 1H-tetrazol-5-yl or $COOR^4$ wherein $R^4$ is hydrogen and X is O.

Another particularly preferred group of compounds are represented by formula I in which $R^1$ and $R^2$ are hydrogen; $R^3$ is 1H-tetrazol-5-yl or $COOR^4$ wherein $R^4$ is hydrogen and X is S or $SO_2$.

The compounds of formula I are prepared by a process comprising:
reacting a compound of formula II

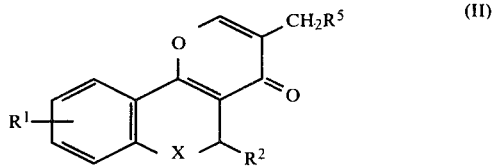

in which $R^1$ is hydrogen, halogen, nitro, trifluoromethyl, lower alkyl or lower alkoxy; $R^2$ is hydrogen or lower alkyl; $R^5$ is chloro, bromo or fluoro; and X is O, S, SO or $SO_2$ with sodium or potassium cyanide to obtain the corresponding compound of formula III

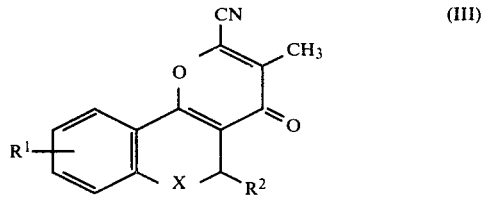

in which $R^1$, $R^2$ and X are as defined herein;

reacting the compound of formula III with sodium azide to obtain the corresponding compound of formula I in which $R^1$, $R^2$ and X are as defined herein and $R^3$ is 1H-tetrazol-5-yl; and if desired, reacting the compound of formula III with a lower alkanol in the presence of an anhydrous mineral acid to obtain the corresponding compound of formula I in which $R^1$, $R^2$ and X are as defined herein and $R^3$ is $COOR^4$ wherein $R^4$ is lower alkyl; and if desired, reacting the latter compound of formula I with sodium or potassium hydroxide to obtain the corresponding compound of formula I in which $R^1$, $R^2$ and X are as defined herein and $R^3$ is $COOR^4$ wherein $R^4$ is hydrogen; and if desired, reacting the compound of formula III with an aqueous solution of sodium or potassium hydroxide to obtain the corresponding compound of formula I in which $R^1$, $R^2$ and X are as defined herein and $R^3$ is hydroxy.

The therapeutically acceptable salts of the compounds of formula I are also included within the scope of this invention.

Another aspect of this invention involves a pharmaceutical composition comprising a compound of formula I, or a therapeutically acceptable addition salt thereof, and a pharmaceutically acceptable carrier.

Still another aspect of this invention involves a method for preventing or treating allergic conditions in a mammal which comprises administering to said mammal an effective allergy alleviating amount of a compound of formula I or a therapeutically acceptable addition salt thereof.

DETAILED DESCRIPTION OF THE INVENTION

The term "lower alkyl" as used herein means straight chain alkyl radicals containing from one to six carbon atoms and branched chain alkyl radicals containing three or four carbon atoms and includes methyl, ethyl, propyl, isopropyl, butyl, isobutyl, pentyl, hexyl and the like.

The term "halo" as used herein means halogens and includes flourine, chlorine, bromine and iodine, unless stated otherwise.

The term "lower alkoxy" as used herein means straight chain alkoxy radicals containing from one to six carbon atoms and branched chain alkoxy radicals containing three or four carbon atoms and includes methoxy, ethoxy, isopropoxy, butoxy, hexyloxy and the like.

The term "lower alkanoyl" as used herein means straight chain alkanoyl radicals containing from two to six carbon atoms and a branched chain alkanoyl radical containing four carbon atoms and includes acetyl, propionyl, isobutyryl, hexanoyl and the like.

The term "lower alkanol" as used herein means both straight and branched chain alkanols containing from one to six carbon atoms and includes methanol, ethanol, isopropanol, butanol, hexanol and the like.

The term "organic proton acceptor" as used herein means the organic bases, or amines for instance, triethylamine, pyridine, N-ethylmorpholine,1,5-diazabicyclo[4.3.0]non-5-ene and the like.

The acidic compounds of formula I in which $R^3$ is hydroxy, 1H-tetrazol-5-yl or $COOR_4$ wherein $R^4$ is hydrogen form salts with suitable therapeutically acceptable inorganic and organic bases. These derived salts possess the same activity as the parent acid and are included within the scope of this invention. The acid is transformed in excellent yield into the corresponding therapeutically acceptable salt by neutralization of said acid with the appropriate inorganic or organic base. The salts are administered in the same manner as the parent acid compounds. Suitable inorganic bases to form these salts include, for example, the hydroxides, carbonates, bicarbonates or alkoxides of the alkali metals or alkaline earth metals, for example, sodium, potassium, magnesium, calcium and the like. Suitable organic bases include the following amines; lower mono-, di- and trialkylamines, the alkyl radicals of which contain up to three carbon atoms, such as methylamine, dimethylamine, trimethylamine, ethylamine, di- and triethylamine, methylethylamine, and the like: mono-, di- and trialkanolamines, the alkanol radicals of which contain up to three carbon atoms, for example, mono-, di- and triethanolamine; alkylene-diamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methyl-morpholine and N-(2-hydroxyethyl)-piperidine, as well as pyridine. Furthermore, there may be mentioned the corresponding quaternary salts, such as the teraalkyl (for example tetramethyl), alkyl-alkanol (for example methyltrimethanol and tri-methyl-monoethanol) and cyclic ammonium salts, for example the N-methylpyridinium, N-methyl-N-(2-hydroxyethyl)-morpholinium N,N-dimethylmorpholinium, N-methyl-N-(2-hydroxyethyl)-morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula I in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acidic compound of formula I is dissolved in a suitable solvent of either moderate or lower polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula I with an equivalent amount of the corresponding quaternary ammonium hydroxide in water solution, followed by evaporation of the water.

Also includes within the scope of this invention are the isomers of the compounds of formula I resulting from the asymmetric centers contained therein.

Also included within the scope of this invention are the tautomeric forms of the compounds of formula I in which $R^4$ is hydroxy resulting from the keto-enol equilibrium contained therein.

ANTI-ALLERGIC ACTIVITY

The compounds of this invention of formula I or therapeutically acceptable salts thereof are useful in the prevention or treatment of allergic reactions in a mammal.

More specifically, the compounds of this invention are useful for the prophylactic treatment as well as for the management of anaphylacetic reactions and atopic allergic manifestations, for example, bronchial asthma, hay fever, allergic rhinitis, allergic conjunctivitis, food allergies, urticaria and the like, in a sensitized mammal.

More specifically exemplified, the compounds of this invention are effective anti-allergic agents when tested using the passive cutaneous anaphylaxis (PCA) method, described by l. Mota, Immumology, 7, 681 (1964). The anti-allergic activity of a given compound is measured in rats by its ability to inhibit the increase in vascular premeability at the site of injection of rat immunoglobulin E (igE) followed by i.v. administration of the specific antigen. Evans blue is injected i.v. at the same time as the specific antigen, and the size of the wheal or of the area infiltrated with Evans blue is measured and compared with that of untreated controls. An effective anti-allergic agent will prevent or inhibit the release of inflammatory mediators (mainly serotonin and histamine from the mast cells) which causes an increase in vascular permeability and thus an infiltration of Evans blue surrounding the site of injection of IgE.

The anti-allergic activity of the compounds of formula I is demonstrated by the reduction of the wheal size of sensitized skin tissue compared to that of control animals. A comparison of the anti-allergic activity of the compounds of this invention with the anti-allergic activity of a standard compound, such as disodium cromoglycate, indicates that the compounds of this invention function in the same manner as disodium cromoglycate by blocking the release of mediators from the mast cells responsible for the allergic reaction.

The following representative compounds of formula I, 3-methyl-2-(1H-tetrazol-5-yl)-4H,5H-[1]-benzothiopyrano[4,3-b]pyran-4-one (described in Example 10) and 3-methyl-4-oxo-2-(1H-tetrazol-5-yl)-4H,5H-[1]benzothiopyrano[4,3-b]pyran-6,6-dioxide (described in Example II), are effective anti-allergic agents in rats by reducing the wheal size by at least 38% and 26%, respectively, at an intraperitoneal dose of 30 mg per kilogram of body weight. Furthermore, the compound of formula I,3-methyl-4-oxo-4H,5H,-[1]-benzothiopyrano[4,3-b]pyran-2-carboxylic acid (described in Example 8), is an effective anti-allergic agent in rats by reducing the wheal size by at least 30% at an intravenous dose of 30 mg per kilogram of body weight. In addition to the compounds of formula I having anti-allergic activity, the intermediates of formula VII are also useful anti-allergic agents. For example, the following compounds of formula VII,3-hydroxymethyl-4H,5H-[1]-benzopyrano-[4,3-b]pyran-4-one (described in Example 3) and 3-hydroxymethyl-4H,5H-[1]-benzothiopyrano[4,3b]pyran4one (described in Examplagents in rats by reducing the wheal size by 58 and 44% respectively, at an intraperitoneal dose of 30 mg per kilogram of body weight.

When the compounds of formula I of this invention are used for suppressing allergic manifestations of anaphylactic reactions and atopic hypersensitivity in a mammal, they are used alone or in combination with pharmacologically acceptable carriers, the proportion of which is determined by the solubility and the chemical nature of the compound, chosen route of administration and standard biological practice. For example, they are administered parenterally by injection; by the nasal route, for instance, as drops or aerosol; or by inhalation from an aerosol.

In addition, the compounds of this invention can be administered in conjunction with common anti-allergic agents, for example, known compounds effecting antihistaminic, analgesic, central nervous system depressant, anti-hypertensive, immunosupressive, anti-bradykinin, anti-serotonin or endocrinological responses.

Therapeutic compositions containing the compounds of this invention are effective anti-allergic agents for preventing or relieving anaphylactic allergic manifestations at dosages of 0.1 mg to 100 mg per kilogram of body weight when administered parenterally to a mammal. For administration to a mammal by parenteral injection, it is preferred to use the compounds of formula I in solution in a sterile aqueous vehicle which may also contain other solutes such as buffers or preservatives, as well as sufficient quantities of pharmaceuticallly acceptable salts or of glucose to make the solution isotonic.

The compounds of formula I can also be administered as nasal powders or insufflations. For such purpose the compounds are administered in finely devided solid from together with a pharmaceutically acceptable solid carrier, for example, a finely divided polyethylene glycol("Carbowax 1540") or finely divided lactose. Such compositions may also contain other excipients in finely divided solid form.

For administering the compounds of this invention by inhalation from an aerosol, the compound of formula I is dissolved in water or ethanol and mixed with a volatile propellant, for example, dichlorotetrafluoroethane and dichlorodifluoromethane, and placed in a pressurized container having a metering valve to release a predetermined amount of material.

The dosage of the compounds of formula I will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstance is reached. In general the compounds of this invention are most desirably administered at a concentration level that will generally afford effective results without causing any harmful or deleterious side effects, and preferably at a level that is in a range of from about 0.1 mg to about 500 mg per kilogram of body weight per day, although as aforementioned variations will occur. However, a dosage level that is in the range from about 0.5 mg to about 200 mg per kilogram of body weight per day is most desirably employed in order to achieve effective results.

Process

For the preparation of the compounds of formula I, the preferred starting materials are the compounds of formula V

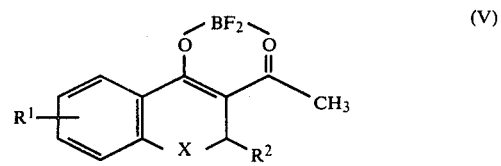

in which $R^1$ is hydrogen, halogen, nitro, trifluoromethyl, lower alkyl or lower alkoxy; $R^2$ is hydrogen or lower alkyl, and X is O, S, SO or $SO_2$.

The compounds of formula V are either known or may be prepared according to known methods, see for example, "Heterocyclic Compounds", R. C. Elderfield, Ed., Vol. 2, John Wiley and Sons, Inc., New York, 1951, pp. 346–354 and 534–535; I. Degani et al., Bull. Sci. Fac. Chim. ind. Bologna, 24, 75 (1966); and W. N. Speckamp, et al., J. Het. Chem., 11, 515 (1974). For example, acylation of a compound of formula IV in which $R^1$, $R^2$ and X are as defined herein, preferably by treatment with boron trifluoride in the presence of acetic anhydride according to the conditions described by D. Kastner, in "Newer Methods of Preparative Organic Chemistry", Academic Press, New York, 1948, pp. 295–297 and R. M. Manyik, et al., J. Amer. Chem. Soc., 75, 5030 (1953), gives the corresponding boron complex of formula V.

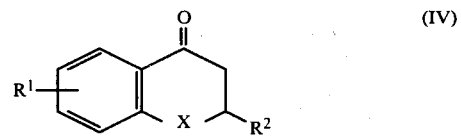

Reaction scheme 1 illustrates the preferred process for the conversion of the starting material V to the intermediate of formula III in which $R^1$, $R^2$ and X are as defined herein Reaction Scheme 1

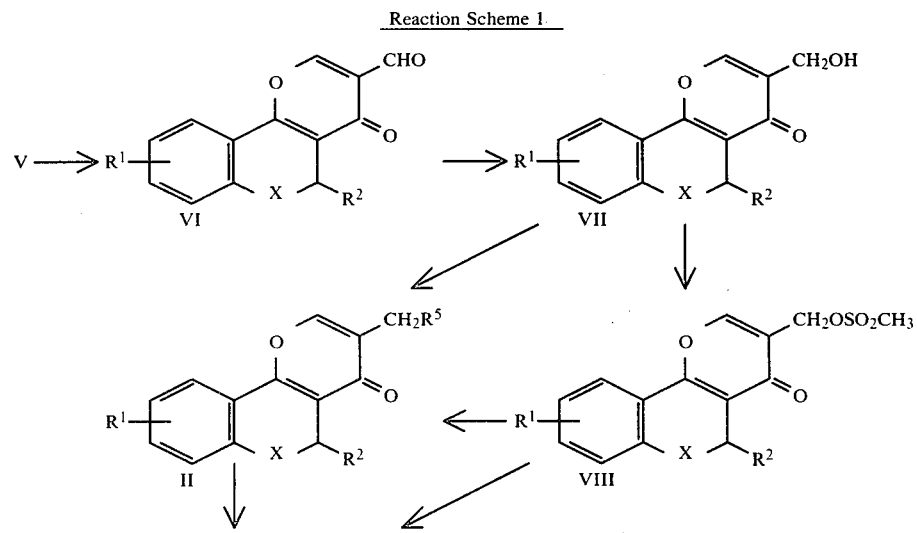

Reaction Scheme 1

-continued

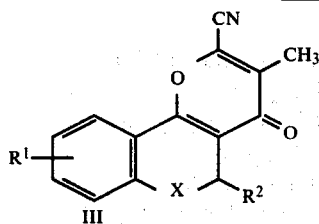

III

With reference to Reaction Scheme 1 the starting material of formula V is reacted with a complex prepared from dimethylformamide and phosphorus oxychloride (Vilsmeier complex) followed by hydrolysis to obtain the corresponding compound of formula VI in which $R^1$, $R^2$ and X are as defined herein. For the latter reaction, about two molar equivalents of phosphorus oxychloride and about ten molar equivalents of dimethylformamide are allowed to react at 0° to 5° C. for about 30 minutes and about one molar equivalent of the compound of formula V is added. The solution is stirred at 0° to 5° C. for 30 minutes, at about 100° C. for two hours and cooled to room temperature. The reaction solution is poured onto crushed ice and the mixture is stirred for about two hours. The compound of formula VI is isolated by filtration or extraction methods. The above described reaction using the Vilsmeier complex is well known for the preparation of $\gamma$-pyrone-3-carboxyaldehydes, for example see the reports by G. A. Reynolds and J. A. Van Allan, J. Het. Chem., 6, 375 (1969) and U.S. Pat. No. 3,862,144, cited above.

The compound of formula VI is reduced with about one to five, preferably 1.1 molar equivalents of sodium borohydride. Preferred reaction condition include the use of methanol as the solvent and temperatures of 0° to 10° C. for 0.5 to two hours. In this manner the corresponding alcohol of formula VII in which $R^1$, $R^2$ and X are as defined herein is obtained.

Reaction of the alcohol of formula VII with a methanesulfonyl chloride, bromide or fluoride, preferably methanesulfonyl chloride, gives the corresponding mesylate of formula VIII in which $R^1$, $R^2$ and X are as defined herein. For this mesylation, about 1.1 molar equivalents of methanesulfonyl chloride, bromide or fluoride is slowly added to a solution of the alcohol of formula VII in a dry inert solvent, preferably methylene chloride, and about 1.5 to 2.0 molar equivalents of an organic proton acceptor, preferably triethylamine, at about 0° to 5° C. After the addition is complete, the reaction mixture is stirred at 0° to 5° C. for 5 to 15 minutes and poured into a mixture of ice and water, from which the mesylate of formula VIII is isolated.

Further reaction of the mesylate of formula VIII with methanesulfonyl chloride, bromide or fluoride, gives the corresponding compound of formula II in which $R^1$, $R^2$ and X are as defined herein and $R^5$ is chloro, bromo or fluoro. This reaction with methanesulfonyl chloride, bromide or fluoride is conducted as follows: a solution of the mesylate of formula VII, an organic proton acceptor (preferably 1.2 to 2.0 molar equivalents of triethylamine) and methanesulfonyl chloride, bromide or fluoride, preferably methanesulfonyl chloride, (1.1 to 10 molar equivalents, preferably two to five molar equivalents) in an inert organic solvent, preferably methylene chloride, is stirred at 20° to 30° C. for about two to ten days and the corresponding compound of formula II in which $R^1$, $R^2$, $R^5$ and X are as defined herein is isolated.

If desired, the compound of formula II can be obtained directly from the alcohol of formula VI by conducting the mesylation of the alcohol of formula VI in the same manner as described immediately above, i.e., at 20° to 30° C. for about two to ten days.

In the next step, a novel reaction for converting $\gamma$-pyrones with a functionality at C-3 (i.e. compounds of formula II and VIII) into their derivatives functionalized at C-2 is described. In this reaction, either of the compounds of formula II or VIII is reacted with about 5 to 15 molar equivalents of sodium or potassium cyanide in a mixture of an inert orgnic solvent and water, preferably about 10 to 30% water in tetrahydrofuran or dioxane, at 20° to 30° C. for 15 to 30 hours to obtain, by a rearrangement, the corresponding compound of formula III in which $R^1$, $R^2$ and X are as defined herein. Although either of the compounds of formula II or VIII can be converted to the corresponding compound of formula III, the preferred method of preparing a compound of formula III is to convert the compound of formula VIII to the compound of formula II and then to react the latter compound with sodium or potassium cyanide. This route to the compound of formula III results in increased yields and easier purifications.

In contrast to the above described rearrangement using sodium or potassium cyanide, the compound of formula VIII, when reacted with cold aqueous dimethylamine, gives the corresponding compound of formula IX in which $R^1$, $R^2$ and X are as defined herein; and the compound of formula II when reacted with aqueous dimethylamine gives the corresponding compound of formula X in which $R^1$, $R^2$ and X are as defined herein.

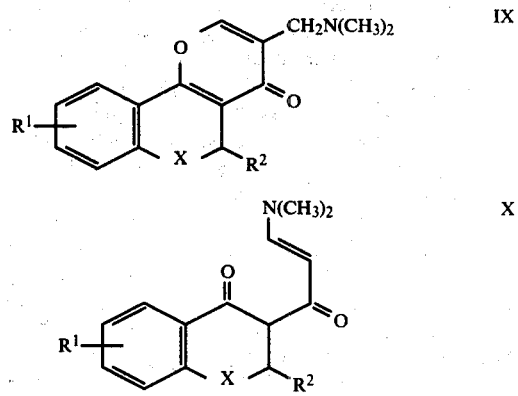

The compounds of formula III, prepared as described above, are readily converted to the compounds of this invention of formula I. In one such conversion, the compound of formula III is reacted with 10 to 50 molar equivalents of sodium or potassium hydroxide in an inert solvent, preferably a mixture of water and a lower alkanol (i.e., methanol or ethanol), at 60° to 100° C. for 15 to 30 hours followed by acidification of the reaction solution, preferably with hydrochloric acid, to obtain the corresponding compound of formula I in which $R^1$, $R^2$ and X are as defined herein and $R^3$ is hydroxy. The latter compound of formula I may also exist in its tautomeric form, as illustrated below.

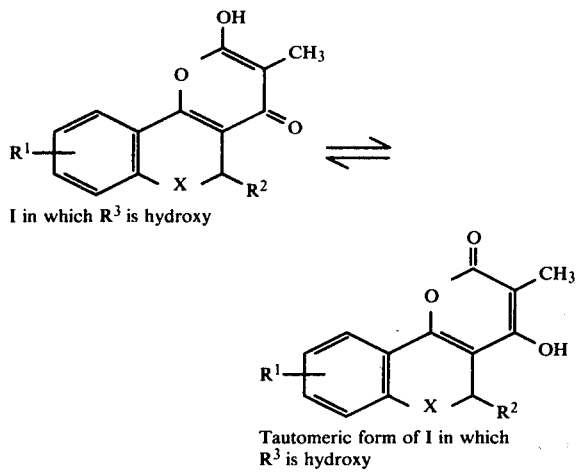

I in which $R^3$ is hydroxy

Tautomeric form of I in which $R^3$ is hydroxy

In another conversion, the compound of formula III is reacted with about 1.1 to 1.5 molar equivalents of sodium or potassium azide and about 0.15 to 0.3 molar equivalents of an acidic buffer, preferably ammonium chloride, in an inert organic solvent, preferably dimethylformamide, at 90° to 130° C. for 10 to 30 hours to obtain the corresponding compound of formula I in which $R^1$, $R^2$ and X are as defined herein and $R^3$ is 1H-tetrazol-5-yl.

In another conversion, the compound of formula III is reacted with 10 to 200 molar equivalents of a lower alkanol in the presence of an anhydrous mineral acid, preferably hydrogen chloride, hydrogen bromide, sulfuric acid or phosphoric acid, at 60° to 100° C. for 5 to 20 hours to obtain the corresponding compound of formula I in which $R^1$, $R^2$ and X are as defined herein and $R^3$ is COOR$^4$ wherein R$^4$ is lower alkyl.

If desired, the latter compound of formula I can be hydrolyzed, preferably with about 5 to 30 molar equivalents of sodium or potassium hydroxide in an aqueous solution of a lower alkanol, preferably methanol or ethanol, at 60° to 100° C. for one to five hours followed by acidification of the reaction mixture with hydrochloric acid, to give the corresponding compound of formula I in which $R^1$, $R^2$ and X are as defined herein and $R^3$ is COOR$^4$ wherein R$^4$ is hydrogen.

If desired, the above described compounds of formula I in which $R^1$, $R^2$ and $R^3$ are as defined herein and X is S can be reacted with about one molar equivalent of m-chloroperbenzoic acid in an inert organic solvent, preferably chloroform, at 15° to 30° C. for 10 to 30 hours to obtain the corresponding compound of formula I in which $R^1$, $R^2$ and $R^3$ are as defined herein and X is SO. The latter reaction can be repeated but using three to five molar equivalents of m-chloroperbenzoic acid to obtain the corresponding compound of formula I in which $R^1$, $R^2$ and $R^3$ are as defined herein and X is $SO_2$.

The following examples illustrate further this invention.

EXAMPLE 1

3-Acetyl-4-chromanone Boron Difluoride Complex (V: $R^1$ and $R^2$=H, and X=O)

A solution of 4-chromanone [35.6g, 0.24 mole, described by S. G. Powell, J. Amer. Chem. Soc., 45, 2711 (1923)] in glacial acetic acid (106 ml) and acetic anhydride (71 ml) is treated in the cold (ice-water cooling) with gaseous boron trifluoride until the solution becomes deep red and precipitation occurs. The mixture is allowed to stand overnight at room temperature. The precipitated solid is collected by filtration, washed with cold glacial acid, dried, and recrystallized from chloroform-hexane to give the title compound (23.2 g), m.p. 197°–198° C.

In the same manner but replacing 4-chromanone with an equivalent amount of 4-thiochromanone, 6-(1-methylpropyl)-4-thiochromanone, 6-butyl-4-thiochromanone, 2-methyl-4-thiochromanone, 6-chloro-4-chromanone, 2-ethyl-8-methyl-4-chromanone, 7-nitro-4-thiochromanone-1-oxide, 5-ethoxy-2-methyl-4-thiochromanone-1,1-dioxide, 2-propyl-7-trifluoromethyl-4-chromanone, 8-bromo-2-(1-methylethyl)-4-thiochromanone, 7-butoxy-4-thiochromanone or 2-butyl-6-hexyl-4-chromanone, the following compounds of formula V are obtained respectively: 3-acetyl-4-thiochromanone boron difluoride complex, mp 183°–185° C., 3-acetyl-6-(1-methylpropyl)-4-thiochromanone boron difluoride complex, mp 107°–109° C., 3-acetyl-6-butyl-4-thiochromanone boron difluoride complex, mp 106°–109° C., 3-acetyl-2-methyl-4-thiochromanone boron difluoride complex, mp 132°–135° C., 3-acetyl-6-chloro-4-chromanone boron difluoride complex, 3-acetyl-2-ethyl-8-methyl-4-chromanone boron difluoride complex, 3-acetyl-7-nitro-4-thiochromanone-1-oxide boron difluoride complex, 3-acetyl-5-ethoxy-2-methyl-4-thiochromanone-1,1-dioxide boron difluoride complex, 3-acetyl-2-propyl-7-trifluoromethyl-4-chromanone boron difluoride complex, 3-acetyl-8-bromo-2-(1-methylethyl)-4-thiochromanone boron difluoride complex, 3-acetyl-7-butoxy-4-thiochromanone boron difluoride complex and 3acetyl-2-butyl-6-hexyl-4-chromanone boron difluoride complex.

EXAMPLE 2

4-Oxo-4H,5H-[1]benzopyrano[4,3-b]pyran-3-carboxaldehyde (VI: $R^1$ and $R^2$=H, and X=O)

Phosphorus oxychloride (3.06 g, 0.02 mole) is added dropwise with ice-cooling to dry dimethylformamide (7.3 g, 0.1 mole). After stirring in the cold for 30 min, 3-acetyl-4-chromanone boron difluoride complex (2.3 g, 0.62 mmoles, described in Example 1) is added in one portion. The reaction mixture is stirred at 0° to 5° C. for 30 min, and at 100° C. for 2 hr. After cooling, the mixture is poured onto crushed ice and the mixture is stirred for 2 hr. The precipitate is collected and washed with water. The precipitate is chromatographed on silica gel using chloroform and the eluates are evaporated. The residue is crystallized from benzene to give crystals (1.5 g) of the title compound, mp 192°–194° C.

In the same manner but replacing 3-acetyl 4-thiochromanone boron difluoride complex with an equivalent amount of another compound of formula V described in Example 1, the following compounds of formula VI are obtained respectively: 4-oxo-4H,5H-[1]benzothiopyrano[4,3-b]pyran-3-carboxaldehyde, mp 141°-143° C., 9-(1-methylpropyl)-4-oxo-4H,5H-[1]benzothiopyrano[4,3-b]pyran-3-carboxaldehyde, mp 94°-96° C., 9-butyl-4-oxo-4H,5H-[1]benzothiopyrano[4,3-b]pyran-3-carboxaldehyde, mp 103°-105° C., 5-methyl-4-oxo-4H,5H-[1]benzothiopyrano[4,3-b]pyran-3-carboxaldehyde, 6-chloro-4-oxo-4H,5H-[1]benzopyrano[4,3-b]pyran-3-carboxaldehyde, 5-ethyl-7-methyl-4-oxo-4H,5H-[1]benzopyrano[4,3-b]pyran-3-carboxaldehyde, 8-nitro-4-oxo-4H,5H-[1]benzothiopyrano[4,3-b]pyran-3-carboxaldehyde-1-oxide, 10-ethoxy-5-methyl-4-oxo-4H,5H-[1]benzothiopyrano[4,3-b]pyran-3-carboxaldehyde-1,1-dioxide, 5-propyl-8-trifluoromethyl-4-oxo-4H,5H-[1]benzopyrano[4,3-b]pyran-3-carboxaldehyde, 7-bromo-5-(1-methylethyl)-4-oxo-4H,5H-[1]benzothiopyrano[4,3-b]pyran-3-carboxaldehyde, 8-butoxy-4-oxo-4H, 5H-[1]benzothiopyrano[4,3-b]pyran-3-carboxaldehyde and 5-butyl-9-hexyl-4-oxo-4H,5H-[1]benzopyrano[4,3-b]pyran-3-carboxaldehyde.

EXAMPLE 3

3-Hydroxymethyl-4H,5H-[1]benzopyrano[4,3-b]pyran-4-one (VII: $R^1$ and $R^2$=H, and X=0)

4-Oxo-4H,5H-[1]benzopyrano[4,3-b]pyran-3-carboxaldehyde (1.12 g, 4.92 mmoles, described in Example 2) is dissolved in hot methanol (200 ml) and the solution is cooled to 0° to 5° C. Sodium borohydride (250 mg, 5.45 mmoles) is added in portions and the mixture is stirred at 0° to 5° C. for one hr. The solvent is evaporated and water is added to the residue. The mixture is extracted with chloroform. The chloroform extract is washed with brine, dried and evaporated. The residue is crystallized from methanol to obtain crystals (0.97 g) of the title compound, mp 188°-190° C.

In the same manner but replacing 4-oxo-4H,5H-[1]benzopyrano[4,3-b]-pyran-3-carboxaldehyde with an equivalent amount of another compound of formula VI described in Example 2, the following compounds of formula VII are obtained respectively: 3-hydroxymethyl-4H,5H-[1]benzothiopyrano[4,3-b]pyran-4-one, mp 147°-149° C., 9-(1-methylpropyl)-3-hydroxymethyl-4H,5H-[1]benzothiopyrano[4,3-b]pyran-4-one, mp 82°-84° C., 9-butyl-3-hydroxymethyl-4H,5H-[1]benzothiopyrano[4,3-b]pyran-4-one, mp 89°-91° C., 5-methyl-3-hydroxymethyl-4H,5H-[1]benzothiopyrano[4,3-b]pyran-4-one, 6-chloro-3-hydroxymethyl-4H,5H-[1]benzopyrano[4,3-b]pyran-4-one, 5-ethyl-17-methyl-3-hydroxymethyl-4H,5H-[1]benzopyrano[4,3-b]pyran-4-one, 10-ethoxy-5-methyl-3-hydroxymethyl-4H,5H-[1]benzothiopyrano[4,3b]pyran-4-one-1,1-dioxide, 5-propyl-8-trifluoromethyl-3-hydroxymethyl-4H,5H-[1]benzopyrano[4,3-b]pyran-4-one, 7-bromo-5-(1-methylethyl)-3-hydroxymethyl-4H,5H-[]benzothiopyrano[4,3-b]pyran-4-one, 8-butoxy-3-hydroxymethyl-4H,5H-[1]benzothiopyrano[4,3-b]pyran-4-one and 5-butyl-9-hexyl-3-hydroxymethyl-4H,5H-[1]benzopyrano[4,3-b]pyran-4-one.

EXAMPLE 4

3-Hydroxymethyl-4-oxo-4H,5H-[1]benzopyrano[4,3-b]pyran-O-methylsulfonate (VIII: $R^1$ and $R^2$=H, and X=O)

To a suspension of 3-hydroxymethyl-4H,5H-[1]benzopyrano[4,3-b]pyran-4-one (1.0 g, 4.34 mmoles, described in Example 3) in dry methylene chloride (70 ml) at 0° C., triethylamine (1 ml, 7.4 mmoles) is added followed by dropwise addition of methanesulfonyl chloride (0.37 ml, 4.7 mmoles). After stirring for a few minutes at 0° C., the reaction mixture is poured into ice-water. The organic layer is separated; washed with cold dilute hydrochloric acid, dilute sodium bicarbonate solution and water; dried and evaporated. The residue is crystallized from chloroform-diethyl ether to obtain crystals (1.0 g) of the title compound, mp 167°-168° C.

In the same manner but replacing 3-hydroxymethyl-4H,5H-[1]benzopyrano-[4,3-b]pyran-4-one with an equivalent amount of another compound of formula VII described in Example 3, the following compounds of formula VIII are obtained respectively: 3-hydroxymethyl-4-oxo-4H,5H-[1]benzothiopyrano[4,3-b]pyran-O-methylsulfonate, mp 138°-139° C., 9-(1-methylpropyl)-3-hydroxymethyl-4-oxo-4H,5H-[1]benzothiopyrano[4,3-b]pyran-O-methylsulfonate,, 9-butyl-3-hydroxymethyl-4-oxo-4H,5H-[1]benzothiopyranO[4,3-b]pyran-O-methylsulfonate, 5-methyl-3-hydroxymethyl-4-oxo-4H,5H-[1]benzothiopyrano[4,3-b]pyran-O-methylsulfonate, 6-chloro-3-hydroxymethyl-4-oxo-4H,5H-[1]benzopyrano[4,3-b]pyran-O-methylsulfonate, 5-ethyl-7-methyl-3-hydroxymethyl-4-oxo-4H,5H-[1]benzopyrano[4,3-b]pyran-O-methylsulfonate, 8-nitro-3-hydroxymethyl-4-oxo-4H,5H-[1]benzothiopyrano[4,3-b]pyran-O-methylsulfonate-1-oxide, 10-ethoxy-5-methyl-3-hydroxymethyl-4-oxo-4H,5H-[1]benzothiopyrano-[4,3-b]pyran-O-methylsulfonate-1,1-dioxide, 5-propyl-8-trifluoromethyl-3-hydroxymethyl-4-oxo-4H,5H-[1]benzopyrano[4,3-b]pyran-O-methylsulfonate, 7-bromo-5-(1-methylethyl)-3-hydroxymethyl-4-oxo-4H,5H-[1]benzothiopyrano[4,3-b]pyran-O-methylsulfonate, 8-butoxy-3-hydroxymethyl-4-oxo-4H,5H-[1]benzothiopyrano[4,3-b]pyran-O-methylsulfonate and 5-butyl-9-hexyl-3-hydroxymethyl-4-oxo-4H,5H-[1]benzopyrano[4,3-b]pyran-O-methylsulfonate.

EXAMPLE 5

3-Chloromethyl-4H,5H-[1]benzopyrano[4,3-b]pyran-4-one(ii: $R^1$ and $R^2$=H, and X=O)

To a suspension of 3-hydroxymethyl-4H,5H-[1]benzopyrano[4,3-b]pyran-4-one(3.7 g, 16.1 mmoles, described in Example 3) in methylene chloride at 0° C., triethylamine (3.7 ml, 27 mmoles) is added followed by dropwise addition of methanesulfonyl chloride (1.3 ml, 16.6 mmoles). The reaction mixture is stirred for 2 days at room temperature and methanesulfonyl chloride (2.6 ml, 23.2 mmoles) is added. The reaction mixture is stirred at room temperature for 18 hr and poured into ice-water. The organic layer is separated; washed with cold dilute hydrochloric acid, dilute sodium bicarbonate solution and water; dried and evaporated. The residue is chromatographed on silica gel using ethyl acetate-benzene (1:9) and the eluates are evaporated to give crystals (3.0 g), mp 162°-164° C. The residue is crystallized from benzene-diethyl ether to obtain the title compound, mp 163°-165° C.

In the same manner but replacing 3-hydroxymethyl-4H,5H-[1]benzopyrano-[4,3-b]pyran-4-one with an equivalent amount of 3-hydroxymethyl-4-oxo-4H,5H-[1]benzopyrano[4,3-b]pyran-O-methylsulfonate, the title compound is obtained.

In the same manner but replacing 3-hydroxymethyl-4H,5H-[1]benzopyrano[4,3-b]pyran-4-one with an equivalent amount of a compound of formula VIII described in Example 4, the following compounds of formula II are obtained respectively: 3-chloromethyl- 4H,5H-[1]benzothiopyrano[4,3-b]pyran-4-one, mp 151°–153° C., 9-(1-methylpropyl)-3-chloromethyl-4H,5H-[1]benzothiopyrano[4,3-b]pyran-4-one, 9-butyl-3-chloromethyl-4H,5H-[1]benzothiopyrano[4,3-b]pyran-4-one, 5-methyl-3-chloromethyl-4H,5H-[1]benzothiopyrano[4,3-b]pyran-4-one, 6-chloro-3-chloromethyl-4H,5H-[1]-benzopyrano[4,3-b]pyran-4-one, 5-ethyl-7-methyl-3-chloromethyl-4H,5H-[1]-benzopyrano[4,3-b]pyran-4-one, 8-nitro-3-chloromethyl-4H,5H-[1]benzothiopyrano[4,3-b]pyran-4-one-1-oxide, 10-ethoxy-5-methyl-3-chloromethyl-4H,5H-[1]benzothiopyrano[4,3-b]pyran-4-one-1,1-dioxide, 5-propyl-8-trifluoromethyl-3-chloromethyl-4H,5H-[1]benzopyrano[4,3-b]pyran-4-one, 7-bromo-5-(1-methylethyl)-3-chloromethyl-4H,5H-[1]benzothiopyrano[4,3-b]pyran-4-one, 8-butoxy-3-chloromethyl-4H,5H-[1]-benzothiopyrano[4,3-b]pyran-4-one and 5-butyl-9-hexyl-3-chloromethyl-4H,5H-[1]-benzopyrano[4,3-b]pyran-4-one.

EXAMPLE 6

3-Methyl-4-oxo-4H,5H-[1]benzopyrano[4,3-b]pyran-2-carbonitrile (III: $R^1$ and $R^2$=H, and X=O)

A solution of 3-chloromethyl-4H,5H-[1]benzopyrano[4,3-b]pyran-4-one (2.65 g, 10.65 mmoles, described in Example 5) in tetrahydrofuran (130 ml) is combined with a solution of sodium cyanide (5.3 g) in water (27 ml). The mixture is stirred overnight at room temperature and poured into water. The solution is extracted with chloroform. The chloroform extract is dried and evaporated. The residue is chromatographed on silica gel using ethyl acetate-benzene (1:19), the eluates are evaporated, and the residue is crystallized from chloroform-diethyl ether to give the title compound (0.767 g), mp 179°–181° C.; nmr (CDCl$_3$) δ 2.25(s, 3H), 5.2(s, 2H), and 6.8–7.7(m, 4H).

In the same manner but replacing 3-chloromethyl-4H,5H-[1]benzopyrano[4,3-b]pyran-4-one with an equivalent amount of 3-hydroxymethyl-4-oxo-4H,5H-[1]benzopyrano[4,3-b]pyran-O-methylsulfonate, the title compound is obtained.

In the same manner but replacing 3-chloromethyl-4H,5H-[1]benzopyrano[4,3-b]pyran-4-one with an equivalent amount of another compound of formula II described in Example 5, the following compounds of formula III are obtained respectively: 3-methyl-4-oxo-4H,5H-[1]benzothiopyrano[4,3-b]pyran-2-carbonitrile, mp 144°–145° C., 3-methyl-9-(1-methylpropyl)-4-oxo-4H,5H-[1]benzothiopyrano[4,3-b]pyran-2-carbonitrile, 9-butyl-3-methyl-4-oxo-4H,5H-[1]benzothiopyrano[4,3-b]pyran-2-carbonitrile, 3,5dimethyl-4-oxo-4H,5H-[1]benzothiopyrano[4,3-b]pyran-2-carbonitrile, 6-chloro-3-methyl-4-oxo-4H,5H-[1]benzopyrano[4,3-b]pyran-2-carbonitrile, 5-ethyl-3,7-dimethyl-4-oxo-4H,5H-[1]benzopyrano[4,3-b]pyran-2-carbonitrile, 8-nitro-3-methyl-4-oxo-4H,5H-[1]benzothiopyrano[4,3-b]pyran-2-carbonitrile-1-oxide, 10-ethoxy-3,5-dimethyl-4-oxo-4H,5H-[1]benzopyrano[4,3-b]pyran-2-carbonitrile-1,1-dioxide, 3-methyl-5-propyl-8-trifluoromethyl-4-oxo-4H,5H-[1]benzopyrano[4,3-b]pyran-2-carbonitrile, 7-bromo-2-methyl-5-(1-methylethyl)-4-oxo-4H,5H-[1]benzothiopyrano[4,3-b]pyran-2-carbonitrile, 8-butoxy-3-methyl-4-oxo-4H,5H-[1]benzothiopyrano[4,3-b]pyran-2-carbonitrile and 5butyl-3-methyl-9-hexyl-4-oxo-4H,5H-[1]benzopyrano[4,3-b]pyran-2-carbonitrile.

EXAMPLE 7

3-Methyl-4-oxo-4H,5H-[1]benzopyrano[4,3-b]pyran-2-carboxylic Acid Methyl Ester (I: $R^1$ and $R^2$=H; $R^3$=COOMe and X=O)

A solution of 3-methyl-4-oxo-4H,5H-[1]benzopyrano[4,3-b]pyran-2-carbonitrile (200 mg, 0.837 mmole, described in Example 6) in methanol is saturated with hydrogen chloride and refluxed for several hr. The solution is evaporated and the residue is partitioned between aqueous sodium bicarbonate and chloroform. The organic phase is separated and the aqueous phase is washed with chloroform. The combined chloroform extracts are dried and evaporated, and the residue is crystallized from methanol to obtain crystals (0.088 g) of the title compound, mp 115°–117° C. The latter crystals are recrystallized from a mixture of chloroform-diethyl ether-pentane to obtain crystals of the title compound, mp 119°–120° C.

In the same manner but replacing 3-methyl-4-oxo-4H,5H-[1]benzopyrano[4,3-b]pyran-2-carbonitrile with an equivalent amount of another compound of formula III described in Example 6, the following compounds of formula I are obtained respectively: 3-methyl-4-oxo-4H,5H-[1]benzothiopyrano[4,3-b]pyran-2-carboxylic acid methyl ester, mp 148°–150° C., 3-methyl-9-(1-methylpropyl)-4-oxo-4,H,5H-[1]benzothiopyrano-[4,3-b]pyran-2-carboxylic acid methyl ester, 9-butyl-3-methyl-4-oxo-4H,5H-[1]-benzothiopyrano[4,3-b]pyran-2-carboxylic acid methyl ester, 3,5-dimethyl-4-oxo-4H,5H-[1]benzothiopyrano[4,3-b]pyran-2-carboxylic acid methyl ester, 6-chloro-3-methyl-4-oxo-4H,5H-[1]benzopyrano[4,3-b]pyran-2-carboxylic acid methyl ester, 5-ethyl-3,7-dimethyl-4-oxo-4H,5H-[1]benzopyrano[4,3-b]pyran-2-carboxylic acid methyl ester, 8-nitro-3-methyl-4-oxo-4H,5H-[1]benzothiopyrano[4,3-b]pyran-2-carboxylic acid methyl ester-1-oxide, 10-ethoxy-3,5-dimethyl-4-oxo-4H,5H-[1]benzothiopyrano[4,3-b]pyran-2-carboxylic acid methyl ester-1,1-dioxide, 3-methyl-5-propyl-8-trifluoromethyl-4-oxo-4H, 5H-[1]benzopyrano[4,3-b]pyran-2-carboxylic acid methyl ester, 7-bromo-3-methyl-5-(1-methylethyl)-4-oxo-4H,5H-[1]benzothiopyrano[4,3-b]pyran-2-carboxylic acid methyl ester, 8-butoxy-3-methyl-4-oxo-4H,5H-[1]benzothiopyrano[4,3-b]pyran-2-carboxylic acid methyl ester and 5-butyl-3-methyl-9-hexyl-4-oxo-4H,5H-[1]benzopyrano[4,3-b]pyran-2-carboxylic acid methyl ester.

EXAMPLE 8

3-Methyl-4-oxo-4H,5H-[1]benzothiopyrano[4,3-b]pyran-2-carboxylic Acid (I: $R^1$ and $R^2$=H, $R^3$=COOH and X=S)

A mixture of 3-methyl-4-oxo-4H,5H-[1]benzothiopyrano[4,3-b]pyran-2-carboxylic acid methyl ester (1.60 g, 5.56 mmoles, described in Example 7) in a solution of sodium hydroxide (0.5 g) in methanol (50 ml) is refluxed for 2 hr and evaporated. The residue is dissolved in water, and the solution is washed with diethyl ether and added with stirring to 3N hydrochloric acid (25 ml). The fine precipitate is collected, washed with very dilute hydrochloric acid, small amount of water and then dried (1.506 g), mp 299°–301° C. The precipitate is crystallized from dimethyl sulfoxide-water to obtain crystals of the title compound, mp 302°–303° C.

A mixture of the latter compound (1.49 g) and 2-ethanolamine in methanol (80 ml) is heated until a solution is obtained. Charcoal is added and the mixture is filtered. The filtrate is concentrated to about 30 ml and diethyl ether is added. The crystals are collected and dried to obtain the 2-aminoethanol salt of the title compound, mp 164°–167° C.

In the same manner but replacing 3-methyl-4-oxo-4H,5H-[1]benzothiopyrano[4,3-b]pyran-2-carboxylic acid methyl ester with an equivalent amount of another compound of formula I described in Example 7, the following compounds of formula I are obtained respectively: 3-methyl-4-oxo-4H,5H-[1]benzopyrano[4,3-b]pyran-2-carboxylic acid, 3-methyl-9-(1-methylpropyl)-4-oxo-4H,5H-[1]benzothiopyrano[4,3-b]pyran-2-carboxylic acid, 9-butyl-3-methyl-4-oxo-4H,5H-[1]benzothiopyrano[4,3-b]pyran-2-carboxylic acid, 3,5-dimethyl-4-oxo-4H,5H-[1]benzothiopyrano[4,3-b]pyran-2-carboxylic acid, 6-chloro-3-methyl-4-oxo-4H,5H-[1]benzopyrano[4,3-b]pyran-2-carboxylic acid, 5-ethyl-3,7-dimethyl-4-oxo-4H,5H-[1]benzopyrano[4,3-b]pyran-2-carboxylic acid, 8-nitro-3-methyl-4-oxo-4H,5H-[1]benzothiopyrano[4,3-b]pyran-2-carboxylic acid-1-oxide, 10-ethoxy-3,5-dimethyl-4-oxo-4H,5H-[1]benzothiopyrano[4,3-b]pyran-2-carboxylic acid-1,1-dioxide, 3-methyl-5-propyl-8-trifluoromethyl-4-oxo-4H,5H-[1]benzopyrano[4,3-b]pyran-2-carboxylic acid, 7-bromo-3-methyl-5-(1-methylethyl)-4-oxo-4H,5H-[1]benzothiopyrano[4,3-b]pyran-2-carboxylic acid, 8-butoxy-3-methyl-4-oxo-4H,5H-[1]benzothiopyrano[4,3-b]pyran-2-carboxylic acid and 5-butyl-3-methyl-9-hexyl-4-oxo-4H,5H-[1]benzopyrano[4,3-b]pyran-2-carboxylic acid.

EXAMPLE 9

3-Methyl-4H,5H-[1]benzothiopyrano[4,3-b]pyran-2,4-dione (I: $R^1$ and $R^2$=H, $R^3$=OH and X=S)

A solution of 3-methyl-4-oxo-4H,5H-[1]benzothiopyrano[4,3-b]pyran-2-carbonitrile (0.255 g, 1 mmole, described in Example 6) in 2.5N aqueous sodium hydroxide (10 ml) and methanol (5 ml) is refluxed overnight. The solution is acidified with hydrochloric acid. The precipitate is collected and dissolved in 1N aqueous sodium hydroxide. The solution is washed with chloroform and acidified with hydrochloric acid. The precipitate is collected and crystallized from methanol to give the title compound (0.070 g), mp 275°–277° C.

In the same manner but replacing 3-methyl-4-oxo-4H,5H-[1]benzothiopyrano[4,3-b]pyran-2-carbonitrile with an equivalent amount of another compound of formula III described in Example 6, the following compounds of formula I are obtained respectively: 3-methyl-4H,5H-[1]benzopyrano[4,3-b]pyran-2,4-dione, mp 279°–281° C., 3-methyl-9-(1-methylpropyl)-4H,5H-[1-benzothiopyrano[4,3-b]pyran-2,4-dione, 9-butyl-3-methyl-4H,5H-[1]benzothiopyrano[4,3-b]pyran-2,4-dione, 3,5-dimethyl-4H,5H-[1]benzothiopyrano[4,3-b]pyran-2,4-dione, 6-chloro-3-methyl-4H,5H-[1]benzopyrano[4,3-b]pyran-2,4-dione, 5-ethyl-3,7-dimethyl-4H,5H-[1]benzopyrano[4,3-b]pyran-2,4-dione, 8-nitro-3-methyl-4H,5H-[1]benzothiopyrano[4,3-b]pyran-2,4-dione-1-oxide, 10-ethoxy-3,5-dimethyl-4H,5H-[1]benzothiopyrano[4,3-b]pyran-2,4-dione-1,1-dioxide, 3-methyl-5-propyl-8-trifluoromethyl-4H,5H-[1]benzopyrano[4,3-b]pyran-2,4-dione, 7-bromo-3-methyl-5-(1-methylethyl)-4H,5H-[1]benzothiopyrano[4,3-b]pyran-2,4-dione, 8-butoxy-3-methyl-4H,5H-[1]benzothiopyrano[4,3-b]pyran-2,4-dione and 5-butyl-3-methyl-9-hexyl-4H,5H-[1]benzopyrano[4,3-b]pyran-2,4-dione.

EXAMPLE 10

3-Methyl-2-(1H-tetrazol-5-yl)-4H,5H-[1]benzothiopyrano[4,3-b]pyran-4-one (I: $R^1$ and $R^2$=H, $R^3$=1H-tetrazol-5-yl and X=S)

A mixture of 3-methyl-4-oxo-4H,5H-[1]benzothiopyrano[4,3-b]pyran-2-carbonitrile (3.14 g, 12.3 mmoles, described in Example 6), sodium azide (0.884 g, 13.6 mmoles) and ammonium chloride (0.130 g, 2.4 mmoles) in dimethylformamide (18 ml) is heated at 110° C. for 18 hr. The dark solution is evaporated and the residue is dissolved in water (50 ml). The aqueous solution is washed with ethyl acetate and acidified with 10% hydrochloric acid. The precipitate is collected, washed with water and crystallized from acetone-water to give the title compound (2.5 g), mp 247°–248° C.

In the same manner but replacing 3-methyl-4-oxo-4H,5H-[1]benzothiopyrano-[4,3-b]pyran-2-carbonitrile with an equivalent amount of another compound of formula III described in Example 6, the following compounds of formula I are obtained respectively: 3-methyl-2-(1H-tetrazol-5-yl)-4H,5H-[1]benzopyrano[4,3-b]pyran-4-one, 3-methyl-9-(1-methylpropyl)-2-(1H-tetrazol-5-yl)-4H,5H-[1]benzothiopyrano[4,3-b]pyran-4-one, 9-butyl-3-methyl-2-(1H-tetrazol-5-yl)-4H,5H-[1]benzothiopyrano[4,3-b]pyran-4-one, 3,5-dimethyl-2-(1H-tetrazol-5-yl)-4H,5H-[1]benzothiopyrano[4,3-b]pyran-4-one, 6-chloro-3-methyl-2-(1H-tetrazol-5-yl)-4H,5H-[1]benzopyrano[4,3-b]pyran-4-one, 5-ethyl-3,7-dimethyl-2-(1H-tetrazol-5-yl)-4H,5H-[1]benzopyrano[4,3-b]pyran-4-one, 8-nitro-3-methyl-2-(1H-tetrazol-5-yl)-4H,5H-[1]benzothiopyrano[4,3-b]pyran-4-one-1-oxide, 10-ethoxy-3,5-dimethyl-2-(1H-tetrazol-5-yl)-4H,5H-[1]benzothiopyrano[4,3-b]pyran-4-one-1,1-dioxide, 3- -methyl-5-propyl-8-trifluoromethyl-2-(1H-tetrazol-5-yl)-4H,5H-[1]benzopyrano[4,3-b]pyran-4-one, 7-bromo-3-methyl-5-(1-methylethyl)-2-(1H-tetrazol-5-yl)-4H,5H-[1]benzothiopyrano[4,3-b]pyrano-4-one, 8-butoxy-3-methyl-2-(1H-tetrazol-5-yl)-4H,5H-[1]benzothiopyrano[4,3-b]pyran-4-one and 5-butyl-3-methyl-9-hexyl-2-(1H-tetrazol-5-yl)-4H,5H-[1]benzopyrano[4,3-b]pyran-4-one.

EXAMPLE 11

3-Methyl-4-oxo-2-(1H-tetrazol-5-yl)-4H,5H-[1]benzothiopyrano[4,3-b]pyran-6,6-dioxide (I: $R^1$ and $R^2$=H, $R^3$=1H-tetrazol-5-yl and X=SO$_2$)

A mixture of 3-methyl-2-(1H-tetrazol-5-yl)-4H,5H-[1]benzothiopyrano[4,3-b]pyran-4-one (1.75 g, 5.30 mmoles, described in Example 10) and m-chloroperbenzoic acid (4.0 g) in chloroform (200 ml) is stirred for 21 hr at room temperature. The precipitate is collected, washed with chloroform and diethyl ether, and crystallized from methanol to give the title compound (1.39 g), mp 268°–270° C.

In the same manner but replacing 3-methyl-2-(1H-tetrazol-5-yl)-4H,5H-[1]benzothiopyrano[4,3-b]pyran-4-one with an equivalent amount of another benzothiopyrano[4,3-b]pyran of formula I described in Example 10, the following compounds of formula I are obtained respectively: 3-methyl-9-(1-methylpropyl)-4-oxo-2-(1H-tetrazol-5-yl)-4H,5H-[1]benzothiopyrano[4,3-b]pyran-6,6-dioxide, 9-butyl-3-methyl-4-oxo-2-(1H-tetrazol-5-yl)-4H,5H-[1]benzothiopyrano[4,3-b]pyran-6,6-dioxide, 3,5-dimethyl-4-oxo-2-(1H-tetrazol-5-yl)-4H,5H-[1]benzothiopyrano[4,3-b]pyran-6,6-dioxide, 8-nitro-3-methyl-4-oxo-2-(1H-tetrazol-5-yl)-4H,5H-[1]benzothiopyrano[4,3-b]pyran-6,6-dioxide, 7-bromo-3-methyl-5-(1-methylethyl)-4-oxo-2-(1H-tetrazol-5-yl)-4H,5H-[1]benzothiopyrano[4,3-b]pyran-6,6-dioxide and 8-butoxy-3-methyl-4-oxo-2-(1H-tetrazol-5-yl)-4H,5H-[1]benzothiopyrano[4,3-b]pyran-6,6-dioxide.

We claim:

1. A compound of formula I

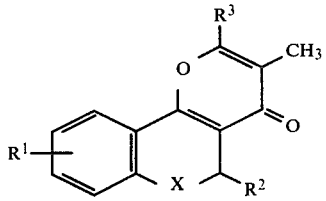
(I)

in which $R^1$ is hydrogen, halogen, nitro, trifluoromethyl, lower alkyl or lower alkoxy; $R^2$ is hydrogen or lower alkyl; $R^3$ is hydroxy, or $COOR^4$ wherein $R^4$ is hydrogen or lower alkyl, and X is S, SO or $SO_2$, or a therapeutically acceptable salt thereof.

2. A compound of formula I, as claimed in claim 1, in which $R^1$ and $R^2$ are as defined therein, $R^3$ is hydroxy and X is S, SO or $SO_2$, or a therapeutically acceptable salt thereof.

3. A compound of formula I, as claimed in claim 1, in which $R^1$ and $R^2$ are as defined therein, $R^3$ is $COOR^4$ wherein $R^4$ is hydrogen or lower alkyl and X is S, SO or $SO_2$, or a therapeutically acceptable salt thereof.

4. A compound of formula I

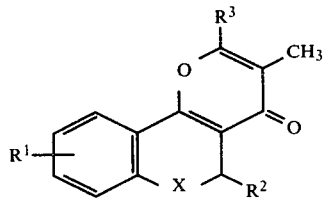
(I)

in which $R^1$ and $R^2$ are hydrogen; $R^3$ is hydroxy, or $COOR^4$ wherein $R^4$ is hydrogen or lower alkyl, and X is S or $SO_2$, or a therapeutically acceptable salt thereof.

5. A compound of formula I

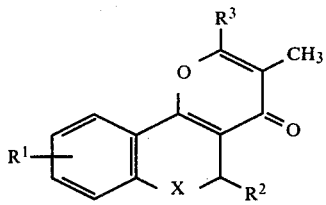
(I)

in which $R^1$ and $R^2$ are hydrogen; $R^3$ is $COOR^4$ wherein $R^4$ is hydrogen and X is S or $SO_2$, or a therapeutically acceptable salt thereof.

6. 3-Methyl-4-oxo-4H,5H-[1]benzothiopyrano[4,3-b]pyran-2-carboxylic acid methyl ester, as claimed in claim 1.

7. 3-Methyl-4-oxo-4H,5H-[1]benzothiopyrano[4,3-b]pyran-2-carboxylic acid, as claimed in claim 1.

8. 3-Methyl-4H,5H-[1]benzothiopyrano[4,3-b]pyran-2,4-dione, as claimed in claim 1.

9. A compound of formula VII

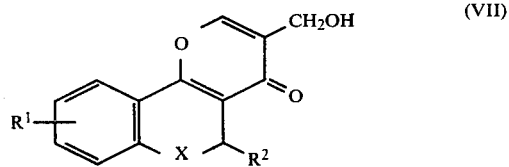
(VII)

in which $R^1$ is hydrogen, halogen, nitro, trifluoromethyl, lower alkyl or lower alkoxy; $R^2$ is hydrogen or lower alkyl, and X is S, SO or $SO_2$.

10. A compound of formula VII, as claimed in claim 9, in which $R^1$ is hydrogen or lower alkyl; $R^2$ is hydrogen and X is S.

11. 3-Hydroxymethyl-4H,5H-[1]benzothiopyrano[4,3-b]pyran-4-one, as claimed in claim 9.

12. 9-(1-Methylpropyl)-3-hydroxymethyl-4H,5H-[1]benzothiopyrano[4,3-b]pyran-4-one, as claimed in claim 9.

13. 9-Butyl-3-hydroxymethyl-4H,5H-[1]benzothiopyrano[4,3-b]pyran-4-one, as claimed in claim 9.

14. A method for preventing or treating allergic conditions in a mammal which comprises administering to said mammal an effective allergy alleviating amount of a compound of formula I or a therapeutically acceptable salt thereof, as claimed in claim 1.

15. A pharmaceutical composition comprising a compound of formula I, or a therapeutically acceptable salt thereof, as claimed in claim 1, and a pharmaceutically acceptable carrier.

* * * * *